United States Patent
Apte et al.

(10) Patent No.: US 10,346,589 B2
(45) Date of Patent: *Jul. 9, 2019

(54) METHOD AND SYSTEM FOR MICROBIOME-DERIVED DIAGNOSTICS AND THERAPEUTICS

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,943

(22) Filed: May 26, 2017

(65) Prior Publication Data

US 2017/0270271 A1 Sep. 21, 2017

Related U.S. Application Data

(63) Continuation of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015.

(51) Int. Cl.
| | | |
|---|---|---|
| *G01N 33/48* | (2006.01) |
| *G06F 19/00* | (2018.01) |
| *G16B 50/00* | (2019.01) |
| *C12Q 1/68* | (2018.01) |
| *C12Q 1/6883* | (2018.01) |
| *C12Q 1/689* | (2018.01) |
| *G16H 50/20* | (2018.01) |
| *G16H 20/10* | (2018.01) |
| *G16B 99/00* | (2019.01) |
| *G16B 5/00* | (2019.01) |
| *G06G 7/58* | (2006.01) |

(52) U.S. Cl.
CPC .......... *G06F 19/3418* (2013.01); *C12Q 1/68* (2013.01); *C12Q 1/689* (2013.01); *C12Q 1/6883* (2013.01); *G06F 19/30* (2013.01); *G16B 5/00* (2019.02); *G16B 50/00* (2019.02); *G16B 99/00* (2019.02); *G16H 20/10* (2018.01); *G16H 50/20* (2018.01); *C12Q 2600/118* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 6,033,864 A | 3/2000 | Braun et al. |
| 6,309,643 B1 | 10/2001 | Braun et al. |
| 6,632,641 B1 | 10/2003 | Brennan et al. |
| 6,861,053 B1 | 3/2005 | Lin et al. |
| D521,843 S | 5/2006 | Hung |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,433,651 B2 | 9/2016 | Jones et al. |
| 9,447,195 B2 | 9/2016 | Cordova et al. |
| 9,506,109 B2 | 11/2016 | Savelkoul et al. |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

"K03100: lepB: signal peptidase I," KEGG, Aug. 7, 2012 (Jul. 8, 2012), p. 1 0f 1. Retrieved from the Internet: on Jun. 12, 2016 (Jun. 12, 2016).

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway? map=map00970&show_description=show. on Jun. 20, 2016 (20.06.

Avila, Maria et al., The Oral Microbiota: Living with a Permanent Guest, DNA and Cell Biology, Nov. 8, 2009, vol. 28, No. 8.

(Continued)

*Primary Examiner* — Eric S Dejong
(74) *Attorney, Agent, or Firm* — Kilpatrick Townsend & Stockton LLP

(57) ABSTRACT

A method for diagnosing and treating an immune microbial dysfunction in a subject, the method comprising: receiving an aggregate set of biological samples from a population of subjects; generating at least one of a microbiome composition dataset and a microbiome functional diversity dataset for the population of subjects; generating a characterization of the immune microbial dysfunction based upon features extracted from at least one of the microbiome composition dataset and the microbiome functional diversity dataset, wherein the characterization is diagnostic of at least one of Crohn's disease, inflammatory bowel disease (IBD), irritable bowel syndrome (IBS), ulcerative colitis, and celiac disease; based upon the characterization, generating a therapy model configured to correct the immune microbial dysfunction; and at an output device associated with the subject, promoting a therapy to the subject based upon the characterization and the therapy model.

20 Claims, 6 Drawing Sheets

(56) References Cited

U.S. PATENT DOCUMENTS

| | | |
|---|---|---|
| 9,663,831 B2 | 5/2017 | Apte et al. |
| 9,703,929 B2 | 7/2017 | Apte et al. |
| 9,710,606 B2 | 7/2017 | Apte et al. |
| 10,242,160 B2 | 3/2019 | Apte et al. |
| 10,246,753 B2 | 4/2019 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold et al. |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0050245 A1 | 2/2015 | Herman et al. |
| 2015/0211055 A1 | 7/2015 | Apte et al. |
| 2015/0211078 A1 | 7/2015 | Apte et al. |
| 2015/0213193 A1 | 7/2015 | Apte et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2016/0228003 A1 | 8/2016 | Apte et al. |
| 2017/0039347 A1 | 2/2017 | Apte et al. |
| 2017/0262608 A1 | 9/2017 | Apte et al. |
| 2017/0268045 A1 | 9/2017 | Apte et al. |
| 2017/0268046 A1 | 9/2017 | Apte et al. |
| 2017/0270268 A1 | 9/2017 | Apte et al. |
| 2017/0270269 A1 | 9/2017 | Apte et al. |
| 2017/0270270 A1 | 9/2017 | Apte et al. |
| 2017/0270272 A1 | 9/2017 | Apte et al. |
| 2017/0286619 A1 | 10/2017 | Apte et al. |
| 2017/0286620 A1 | 10/2017 | Apte et al. |
| 2019/0019575 A1 | 1/2019 | Apte et al. |

FOREIGN PATENT DOCUMENTS

| | | |
|---|---|---|
| EP | 2994756 | 3/2016 |
| WO | 050513 | 4/2012 |
| WO | 2013/176774 A1 | 11/2013 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2015095241 | 12/2015 |
| WO | 2016065075 | 4/2016 |
| WO | 2016/070151 A1 | 5/2016 |
| WO | 138337 | 9/2016 |
| WO | 172643 | 10/2016 |
| WO | 044902 | 3/2017 |

OTHER PUBLICATIONS

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Jan. 4, 2012), vol. 13, pp. 260-270.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. elongata in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594.

Kanehisa et al. "KEGG: Kyoto encyclopedia of genes and genomes,"Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.

Ponnusamy et al. "Microbial community and metabolomic comparison of irritable bowel syndrome faeces," Feb. 17, 2011 (Feb. 17, 2011), vol. 60, pp. 817-827. entire document.

U.S. Appl. No. 14/919,614 , "Non-Final Office Action", dated Jul. 14, 2016, 10 pages.

U.S. Appl. No. 14/919,614 , "Notice of Allowance", dated May 19, 2017, 10 pages.

U.S. Appl. No. 15/606,743 , "Non Final Office Action", dated Dec. 19, 2017, 10 pages.

U.S. Appl. No. 15/606,743 , "Notice of Allowance", dated Sep. 20, 2018, 5 pages.

U.S. Appl. No. 15/606,824 , "Final Office Action", dated Sep. 20, 2018, 8 pages.

U.S. Appl. No. 15/606,824 , "Non Final Office Action", dated Jan. 16, 2018, 10 pages.

U.S. Appl. No. 15/606,874 , "Final Office Action", dated Aug. 31, 2018, 8 pages.

U.S. Appl. No. 15/606,874 , "Non-Final Office Action", dated Feb. 9, 2018, 10 pages.

U.S. Appl. No. 15/606,874 , "Notice of Allowance", dated Jan. 17, 2019, 5 pages.

U.S. Appl. No. 15/606,909 , "Final Office Action", dated Sep. 20, 2018, 8 pages.

U.S. Appl. No. 15/606,909 , "Non Final Office Action", dated Mar. 9, 2018, 10 pages.

U.S. Appl. No. 15/606,909 , "Notice of Allowance", dated Feb. 20, 2019, 5 pages.

U.S. Appl. No. 15/606,975 , "Final Office Action", dated Jun. 14, 2018, 8 pages.

U.S. Appl. No. 15/606,975 , "Non-Final Office Action", dated Sep. 25, 2017, 10 pages.

(56) References Cited

OTHER PUBLICATIONS

U.S. Appl. No. 15/606,975 , "Notice of Allowance", dated Oct. 19, 2018, 5 pages.
U.S. Appl. No. 15/621,144 , "Final Office Action", dated Nov. 1, 2018, 7 pages.
U.S. Appl. No. 15/621,144 , "Non Final Office Action", dated Apr. 10, 2018, 10 pages.
U.S. Appl. No. 15/621,152 , "Final Office Action", dated Nov. 1, 2018, 7 pages.
U.S. Appl. No. 15/621,152 , "Non-Final Office Action", dated Apr. 10 2018, 10 pages.
U.S. Appl. No. 16/084,946 , "U.S. Patent Application No.", Method and System for Microbiome-Derived Diagnostics and Therapeutics for Conditions Associated With Gastrointestinal Health, Sep. 13, 2018.
CA2,962,466 , "Examination Report", dated Mar. 23, 2018, 4 pages.
EP15852829.9 , "Examination Report", dated May 14, 2018, 4 pages.
EP15852829.9 , "Supplementary European Search Report", dated May 14, 2018, 2 pages.
Kinross et al., "Gut Microbiome-host Interactions in Health and Disease", Genome Medicine, vol. 3, No. 14, 2011, 12 pages.
Morgan et al., "Biodiversity and Functional Genomics in the Human Microbiome", Trends Genet., vol. 29, No. 1, Jan. 2013, pp. 51-58.
PCT/US2015/056767 , "International Preliminary Report on Patentability", dated May 4, 2017, 9 pages.
PCT/US2015/056767 , "International Search Report and Written Opinion", dated Jan. 11, 2016, 10 pages.
Arat, et al., "Microbiome Changes in Healthy Volunteers Treated With Gsk1322322, A Novel Antibiotic Targeting Bacterial Peptide Deformylase", Antimicrobial Agents and Chemotherapy, vol. 59, No. 2, Feb. 2015, pp. 1182-1192.
Bjerketorp, et al., "Rapid Lab-On-A-Chip Profiling of Human Gut Bacteria", Journal of Microbiological Methods, vol. 72, 2008, pp. 82-90.
European Application No. 16845213.4, Extended European Search Report and Opinion dated Apr. 9, 2019, 12 pages.
International Application No. PCT/US2017/052098, International Preliminary Report on Patentability dated Mar. 28, 2019, 9 pages.
International Application No. PCT/US2017/042015, International Preliminary Report on Patentability dated Jan. 24, 2019, 11 pages.
U.S. Appl. No. 15/098,110, Notice of Allowance dated Mar. 7, 2019, 7 pages.
U.S. Appl. No. 15/098,153, Notice of Allowance dated Feb. 21, 2019, 8 pages.
U.S. Appl. No. 15/098,174, Notice of Allowance dated Jan. 24, 2019, 7 pages.
U.S. Appl. No. 15/098,222, Notice of Allowance dated Apr. 3, 2019, 5 pages.
U.S. Appl. No. 15/098,236, Notice of Allowance dated Apr. 3, 2019, 7 pages.
U.S. Appl. No. 15/203,589, Notice of Allowance dated Apr. 3, 2019, 7 pages.
U.S. Appl. No. 15/204,707, Notice of Allowance dated Apr. 3, 2019, 7 pages.
U.S. Appl. No. 15/207,897, Final Office Action dated Jan. 18, 2019, 7 pages.
U.S. Appl. No. 15/207,930, Final Office Action dated Jan. 31, 2019, 8 pages.
U.S. Appl. No. 15/294,482, Non-Final Office Action dated Feb. 21, 2019, 13 pages.
U.S. Appl. No. 15/294,526, Non-Final Office Action dated Feb. 21, 2019, 12 pages.
U.S. Appl. No. 15/374,890, Non-Final Office Action dated Mar. 7, 2019, 12 pages.
U.S. Appl. No. 15/452,529, Notice of Allowability dated Mar. 6, 2019, 2 pages.
U.S. Appl. No. 15/606,824, Notice of Allowance dated Mar. 26, 2019, 5 pages.
U.S. Appl. No. 15/606,975, Notice of Allowance dated Apr. 3, 2019, 5 pages.
U.S. Appl. No. 15/621,144, Notice of Allowance dated Mar. 8, 2019, 6 pages.
U.S. Appl. No. 15/621,152, Notice of Allowance dated Mar. 8, 2019, 6 pages.
U.S. Appl. No. 15/621,187, Final Office Action dated Feb. 21, 2019, 7 pages.
U.S. Appl. No. 15/621,363, Notice of Allowance dated Mar. 21, 2019, 5 pages.
U.S. Appl. No. 15/621,378, Notice of Allowance dated Mar. 7, 2019, 5 pages.
U.S. Appl. No. 15/621,398, Notice of Allowance dated Mar. 21, 2019, 5 pages.
U.S. Appl. No. 15/621,420, Notice of Allowance dated Feb. 25, 2019, 5 pages.
U.S. Appl. No. 15/621,445, Notice of Allowance dated Mar. 21, 2019, 5 pages.
U.S. Appl. No. 15/636,015, Notice of Allowance dated Apr. 3, 2019, 5 pages.
U.S. Appl. No. 15/644,612, Notice of Allowance dated Mar. 21, 2019, 5 pages.
U.S. Appl. No. 15/644,628, Notice of Allowance dated Mar. 21, 2019, 5 pages.
U.S. Appl. No. 15/645,008, Notice of Allowance dated Mar. 22, 2019, 5 pages.
U.S. Appl. No. 15/645,034, Notice of Allowance dated Mar. 25, 2019, 7 pages.
U.S. Appl. No. 15/645,049, Notice of Allowance dated Mar. 20, 2019, 5 pages.
U.S. Appl. No. 15/645,062, Notice of Allowance dated Mar. 20, 2019, 5 pages.
U.S. Appl. No. 15/645,076, Notice of Allowance dated Mar. 22, 2019, 5 pages.
U.S. Appl. No. 15/645,102, Notice of Allowance dated Mar. 20, 2019, 5 pages.
U.S. Appl. No. 15/655,640, Notice of Allowance dated Apr. 3, 2019, 5 pages.
U.S. Appl. No. 15/664,067, Non-Final Office Action dated Apr. 5, 2019, 13 pages.
U.S. Appl. No. 15/815,365, Notice of Allowance dated Apr. 3, 2019, 5 pages.
U.S. Appl. No. 15/815,622, Notice of Allowance dated Apr. 3, 2019, 5 pages.
U.S. Appl. No. 15/815,636, Notice of Allowance dated Apr. 3, 2019, 5 pages.
U.S. Appl. No. 15/815,995, Notice of Allowance dated Apr. 3, 2019, 5 pages.
U.S. Appl. No. 15/816,041, Notice of Allowance dated Apr. 3, 2019, 5 pages.
U.S. Appl. No. 15/819,190, Notice of Allowance dated Apr. 3, 2019, 5 pages.
U.S. Appl. No. 15/844,139, Notice of Allowance dated Apr. 3, 2019, 5 pages.
U.S. Appl. No. 15/844,360, Notice of Allowance dated Apr. 3, 2019, 5 pages.
U.S. Appl. No. 15/845,190, Notice of Allowance dated Apr. 3, 2019, 5 pages.
U.S. Appl. No. 15/848,779, Notice of Allowance dated Apr. 3, 2019, 5 pages.
U.S. Appl. No. 15/848,824, Notice of Allowance dated Apr. 3, 2019, 5 pages.
U.S. Appl. No. 15/848,985, Notice of Allowance dated Apr. 3, 2019, 5 pages.
U.S. Appl. No. 15/849,041, Notice of Allowance dated Apr. 3, 2019, 5 pages.
U.S. Appl. No. 15/849,110, Notice of Allowance dated Apr. 3, 2019, 5 pages.
U.S. Appl. No. 15/849,186, Notice of Allowance dated Apr. 3, 2019, 5 pages.
U.S. Appl. No. 15/997,654, Notice of Allowance dated Apr. 4, 2019, 6 pages.

(56) References Cited

OTHER PUBLICATIONS

U.S. Appl. No. 16/124,108, Non-Final Office Action dated Mar. 8, 2019, 12 pages.

US 10,346,589 B2

METHOD AND SYSTEM FOR MICROBIOME-DERIVED DIAGNOSTICS AND THERAPEUTICS

CROSS-REFERENCE TO RELATED APPLICATIONS

This application is a continuation of U.S. application Ser. No. 14/919,614, filed 21 Oct. 2017, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

TECHNICAL FIELD

This invention relates generally to the field of microbiology and more specifically to a new and useful method and system for microbiome-derived diagnostics and therapeutics in the field of microbiology.

BACKGROUND

A microbiome is an ecological community of commensal, symbiotic, and pathogenic microorganisms that are associated with an organism. The human microbiome comprises over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects have not been viable due to limitations in current technologies.

As such, there is a need in the field of microbiology for a new and useful method and system for characterizing health conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. First Method

Figure 1A:
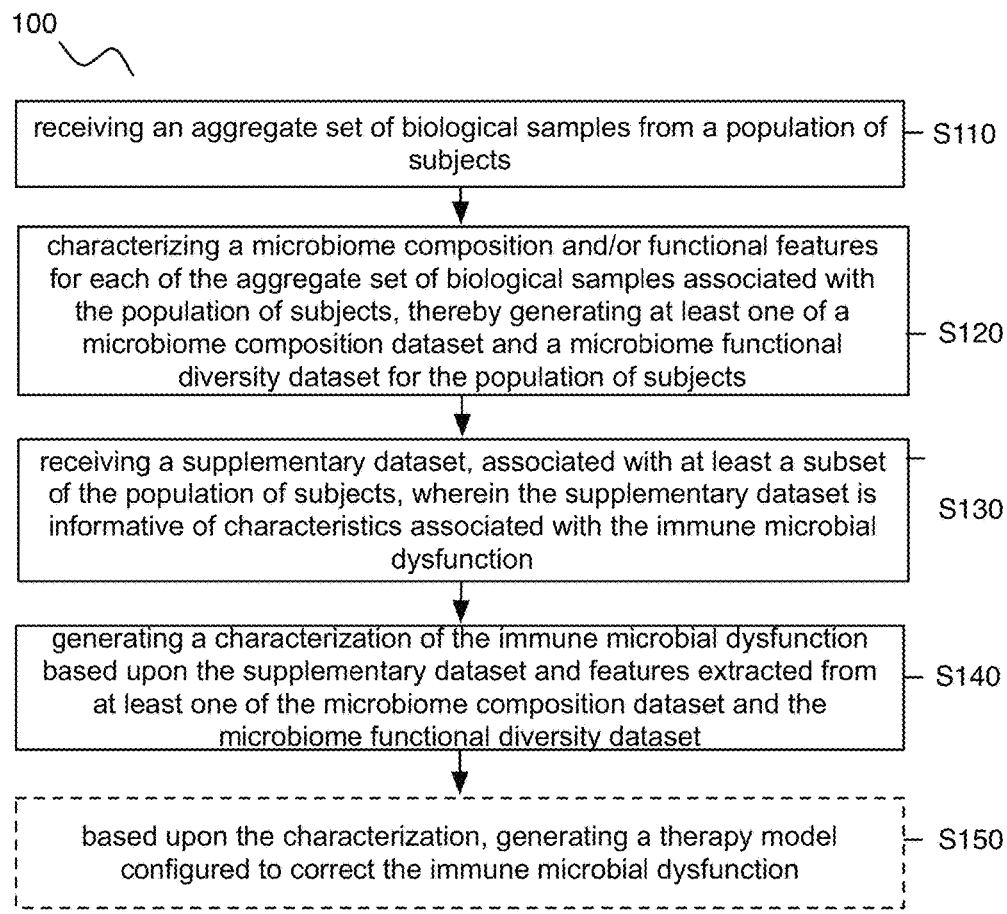
FIG. 1A is a flowchart of an embodiment of a first method for generating microbiome-derived diagnostics and therapeutics.

As shown in FIG. 1A, a first method 100 for diagnosing and treating an immune microbial dysfunction comprises: receiving an aggregate set of biological samples from a population of subjects S110; characterizing a microbiome composition and/or functional features for each of the aggregate set of biological samples associated with the population of subjects, thereby generating at least one of a microbiome composition dataset and a microbiome functional diversity dataset for the population of subjects S120; receiving a supplementary dataset, associated with at least a subset of the population of subjects, wherein the supplementary dataset is informative of characteristics associated with the immune microbial dysfunction S130; and generating a characterization of the immune microbial dysfunction based upon the supplementary dataset and features extracted from at least one of the microbiome composition dataset and the microbiome functional diversity dataset S140. In some variations, the first method 100 can further include: based upon the characterization, generating a therapy model configured to correct the immune microbial dysfunction S150.

The first method 100 functions to generate models that can be used to characterize and/or diagnose subjects according to at least one of their microbiome composition and functional features (e.g., as a clinical diagnostic, as a companion diagnostic, etc.), and provide therapeutic measures (e.g., probiotic-based therapeutic measures, phage-based therapeutic measures, small-molecule-based therapeutic measures, clinical measures, etc.) to subjects based upon microbiome analysis for a population of subjects. As such, data from the population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states. Variations of the method 100 can further facilitate monitoring and/or adjusting of therapies provided to a subject, for instance, through reception, processing, and analysis of additional samples from a subject throughout the course of therapy. In specific examples, the method 100 can be used to promote targeted therapies to subjects suffering from an immune microbial dysfunction. In specific examples, the method 100 can be used for characterization of and/or therapeutic intervention for one or more of: Crohn's disease, inflammatory bowel disease (IBD), irritable bowel syndrome (IBS), ulcerative colitis, and celiac disease.

Figure 1B:
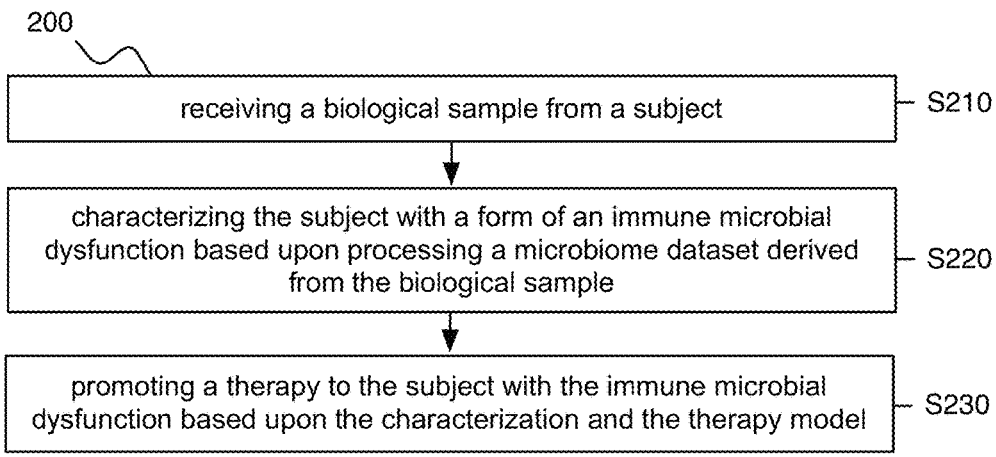
FIG. 1B is a flowchart of an embodiment of a second method for generating microbiome-derived diagnostics and therapeutics.

As such, in some embodiments, outputs of the first method 100 can be used to generate diagnostics and/or provide therapeutic measures for a subject based upon an analysis of the subject's microbiome composition and/or functional features of the subject's microbiome. Thus, as shown in FIG. 1B, a second method 200 derived from at least one output of the first method 100 can include: receiving a biological sample from a subject S210; characterizing the subject with a form of an immune microbial dysfunction based upon processing a microbiome dataset derived from the biological sample S220; and promoting a therapy to the subject with the immune microbial dysfunction based upon the characterization and the therapy model S230. Embodiments, variations, and examples of the second method 200 are described in more detail below.

The methods 100, 200 function to generate models that can be used to classify individuals and/or provide therapeutic measures (e.g., therapy recommendations, therapies, therapy regimens, etc.) to individuals based upon microbiome analysis for a population of individuals. As such, data from the population of individuals can be used to generate models that can classify individuals according to their microbiome compositions (e.g., as a diagnostic measure), indicate states of health and areas of improvement based upon the classification(s), and/or provide therapeutic measures that can push the composition of an individual's microbiome toward one or more of a set of improved equilibrium states. Variations of the second method 200 can further facilitate monitoring and/or adjusting of therapies provided to an individual, for instance, through reception, processing, and analysis of additional samples from an individual throughout the course of therapy.

Figure 2:
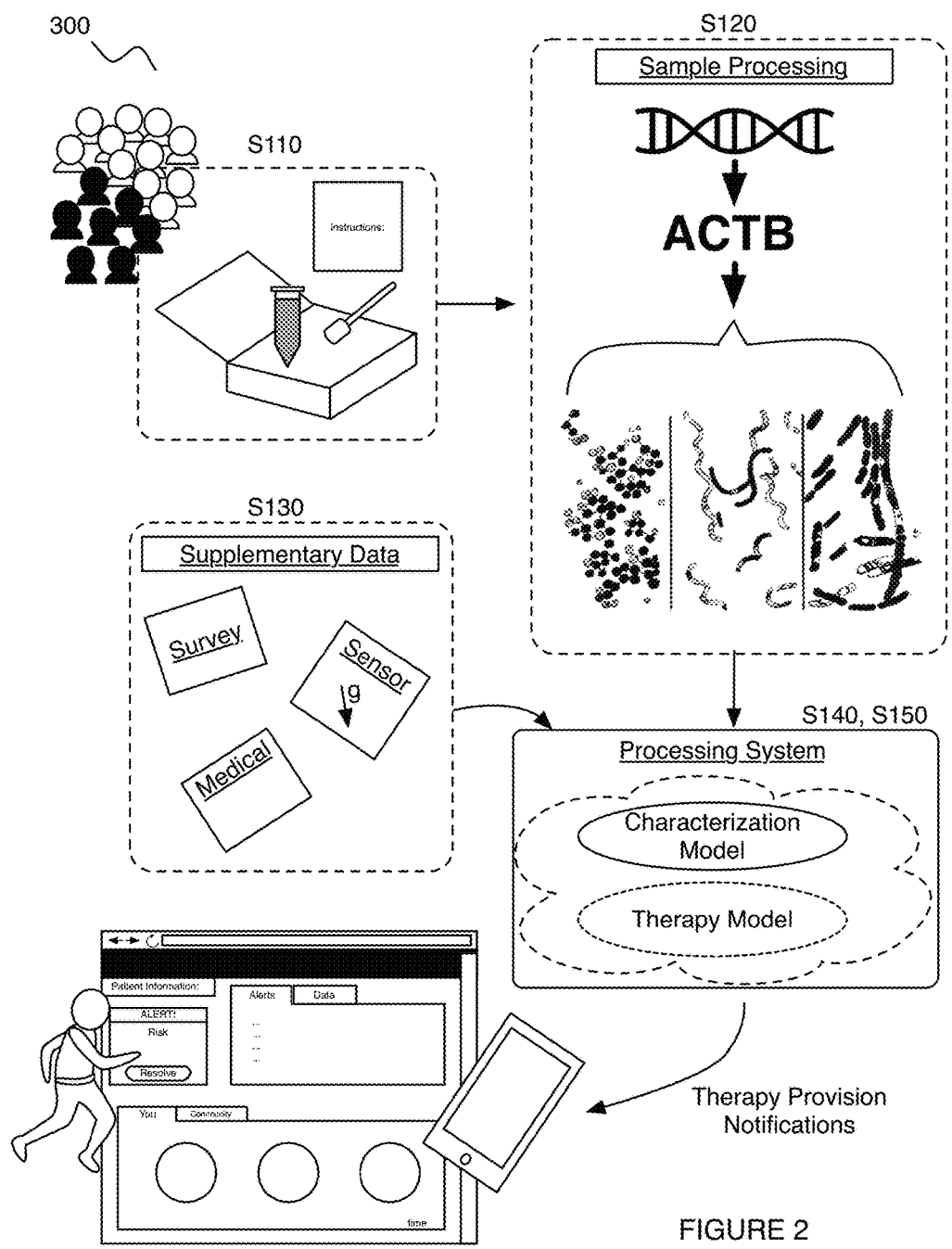
FIG. 2 depicts an embodiment of a method and system for generating microbiome-derived diagnostics and therapeutics.

In one application, at least one of the methods 100, 200 is implemented, at least in part, at a system 300, as shown in FIG. 2, that receives a biological sample derived from the subject (or an environment associated with the subject) by way of a sample reception kit, and processes the biological sample at a processing system implementing a characterization process and a therapy model configured to positively influence a microorganism distribution in the subject (e.g., human, non-human animal, environmental ecosystem, etc.). In variations of the application, the processing system can be configured to generate and/or improve the characterization process and the therapy model based upon sample data received from a population of subjects. The method 100 can, however, alternatively be implemented using any other suitable system(s) configured to receive and process microbiome-related data of subjects, in aggregation with other information, in order to generate models for microbiome-derived diagnostics and associated therapeutics. Thus, the method 100 can be implemented for a population of subjects (e.g., including the subject, excluding the subject), wherein the population of subjects can include patients dissimilar to and/or similar to the subject (e.g., in health condition, in dietary needs, in demographic features, etc.). Thus, information derived from the population of subjects can be used to provide additional insight into connections between behaviors of a subject and effects on the subject's microbiome, due to aggregation of data from a population of subjects.

Thus, the methods 100, 200 can be implemented for a population of subjects (e.g., including the subject, excluding the subject), wherein the population of subjects can include subjects dissimilar to and/or similar to the subject (e.g., health condition, in dietary needs, in demographic features, etc.). Thus, information derived from the population of subjects can be used to provide additional insight into connections between behaviors of a subject and effects on the subject's microbiome, due to aggregation of data from a population of subjects.

1.1 First Method: Sample Handling

Block S110 recites: receiving an aggregate set of biological samples from a population of subjects, which functions to enable generation of data from which models for characterizing subjects and/or providing therapeutic measures to subjects can be generated. In Block S110, biological samples are preferably received from subjects of the population of subjects in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of an subject's body, and any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), and tissue samples.

In the above variations and examples, samples can be taken from the bodies of subjects without facilitation by another entity (e.g., a caretaker associated with an individual, a health care professional, an automated or semi-automated sample collection apparatus, etc.), or can alternatively be taken from bodies of individuals with the assistance of another entity. In one example, wherein samples are taken from the bodies of subjects without facilitation by another entity in the sample extraction process, a sample-provision kit can be provided to a subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the individual to be delivered to a sample processing operation (e.g., by a mail delivery system). In another example, wherein samples are extracted from the user with the help of another entity, one or more samples can be collected in a clinical or research setting from a subject (e.g., during a clinical appointment).

In Block S110, the aggregate set of biological samples is preferably received from a wide variety of subjects, and can involve samples from human subjects and/or non-human subjects. In relation to human subjects, Block S110 can include receiving samples from a wide variety of human subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), biomarker states (e.g., cholesterol levels, lipid levels, etc.), weight, height, body mass index, genotypic factors, and any other suitable trait that has an effect on microbiome composition. As such, as the number of subjects increases, the predictive power of feature-based models generated in subsequent blocks of the method 100 increases, in relation to characterizing of a variety of subjects based upon their microbiomes. Additionally or alternatively, the aggregate set of biological samples received in Block S110 can include receiving biological samples from a targeted group of similar subjects in one or more of: demographic traits, health conditions, living situations, dietary habits, behavior tendencies, levels of mobility, and any other suitable trait that has an effect on microbiome composition.

In some embodiments, receiving the aggregate set of biological samples in Block S110 can be performed according to embodiments, variations, and examples of sample reception as described in U.S. application Ser. No. 14/593,424 filed on 9 Jan. 2015 and entitled "Method and System for Microbiome Analysis", which is incorporated herein in its entirety by this reference. However, receiving the aggregate set of biological samples in Block S110 can additionally or alternatively be performed in any other suitable manner. Furthermore, some variations of the first method 100 can omit Block S110, with processing of data derived from a set of biological samples performed as described below in subsequent blocks of the method 100.

1.2 First Method: Sample Analysis, Microbiome Composition, and Functional Aspects Block S120 recites: characterizing a microbiome composition and/or functional features for each of the aggregate set of biological samples associated with a population of subjects, thereby generating at least one of a microbiome composition dataset and a microbiome functional diversity dataset for the population of subjects. Block S120 functions to process each of the aggregate set of biological samples, in order to determine compositional and/or functional aspects associated with the microbiome of each of a population of subjects. Compositional and functional aspects can include compositional aspects at the microorganism level, including parameters related to distribution of microorgansims across different groups of kingdoms, phyla, classes, orders, families, genera, species, subspecies, strains, infraspecies taxon (e.g., as measured in total abundance of each group, relative abundance of each group, total number of groups represented, etc.), and/or any other suitable taxa. Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g., enzyme activities, transport functions, immune activities, etc.). Outputs of Block S120 can thus be used to provide features of interest for the characterization process of Block S140, wherein the features can be microorganism-based (e.g., presence of a genus of bacteria), genetic-based (e.g., based upon representation of specific genetic regions and/or sequences) and/or functional-based (e.g., presence of a specific catalytic activity, presence of metabolic pathways, etc.).

In one variation, Block S120 can include characterization of features based upon identification of phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L13, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase alpha subunit, phenylalanyl-tRNA synthetase beta subunit, tRNA pseudouridine synthase B, porphobilinogen deaminase, phosphoribosylformylglycinamidine cyclo-ligase, and ribonuclease HIII. However, the markers can include any other suitable marker(s)

Characterizing the microbiome composition and/or functional features for each of the aggregate set of biological samples in Block S120 thus preferably includes a combination of sample processing techniques (e.g., wet laboratory techniques) and computational techniques (e.g., utilizing tools of bioinformatics) to quantitatively and/or qualitatively characterize the microbiome and functional features associated with each biological sample from a subject or population of subjects.

In variations, sample processing in Block S120 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. Thus, portions of Block S120 can be implemented using embodiments, variations, and examples of the sample handling network and/or computing system as described in U.S. application Ser. No. 14/593,424 filed on 9 Jan. 2015 and entitled "Method and System for Microbiome Analysis", which is incorporated herein in its entirety by this reference. Thus the computing system implementing one or more portions of the method 100 can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, Block S120 can be performed using any other suitable system(s).

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S120 can involve chemical methods (e.g., using a detergent, using a solvent, using a surfactant, etc.). Additionally or alternatively, lysing or disrupting in Block S120 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, performing an amplification operation S123 on purified nucleic acids can include performing one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Primers used in variations of Block S110 can additionally or alternatively include incorporated barcode sequences specific to each biological sample, which can facilitate identification of biological samples post-amplification. Primers used in variations of Block S110 can additionally or alternatively include adaptor regions configured to cooperate with sequencing techniques involving complementary adaptors (e.g., according to protocols for Illumina Sequencing).

Identification of a primer set for a multiplexed amplification operation can be performed according to embodiments, variations, and examples of methods described in U.S. App. No. 62/206,654 filed 18 Aug. 2015 and entitled "Method and System for Multiplex Primer Design", which is herein incorporated in its entirety by this reference. Performing a multiplexed amplification operation using a set of primers in Block S123 can additionally or alternatively be performed in any other suitable manner.

Figure 3:
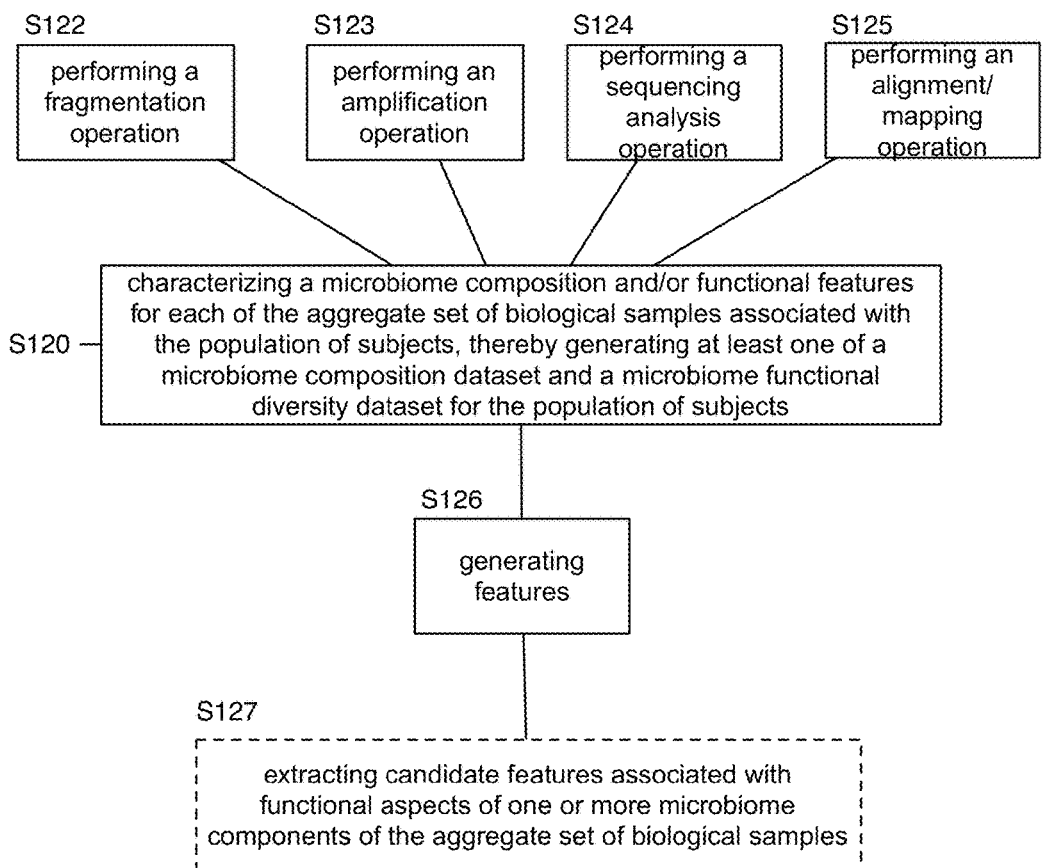
FIG. 3 depicts variations of a portion of an embodiment of a method for generating microbiome-derived diagnostics and therapeutics.

Additionally or alternatively, as shown in FIG. 3, Block S120 can implement any other step configured to facilitate processing (e.g., using a Nextera kit) for performance of a fragmentation operation S122 (e.g., fragmentation and tagging with sequencing adaptors) in cooperation with the amplification operation S123 (e.g., S122 can be performed after S123, S122 can be performed before S123, S122 can be performed substantially contemporaneously with S123, etc)

Furthermore, Blocks S122 and/or S123 can be performed with or without a nucleic acid extraction step. For instance, extraction can be performed prior to amplification of nucleic acids, followed by fragmentation, and then amplification of fragments. Alternatively, extraction can be performed, followed by fragmentation and then amplification of fragments. As such, in some embodiments, performing an amplification operation in Block S123 can be performed according to embodiments, variations, and examples of amplification as described in U.S. application Ser. No. 14/593,424 filed on 9 Jan. 2015 and entitled "Method and System for Microbiome Analysis". Furthermore, amplification in Block S123 can additionally or alternatively be performed in any other suitable manner.

In a specific example, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an Illumina forward index for MiSeq/NextSeq/HiSeq platforms) or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, and a sequence for targeting a specific target region (e.g., 16S region, 18S region, ITS region). Amplification and sequencing can further be performed on any suitable amplicon, as indicated throughout the disclosure. In the specific example, sequencing comprises Illumina sequencing (e.g., with a HiSeq platform, with a MiSeq platform, with a NextSeq platform, etc.) using a sequencing-by-synthesis technique.

Some variations of sample processing in Block S120 can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S120 can include any one or more of: performing a sequencing analysis operation S124 including identification of microbiome-derived sequences (e.g., as opposed to subject sequences and contaminants), performing an alignment and/or mapping operation S125 of microbiome-derived sequences (e.g., alignment of fragmented sequences using one or more of single-ended alignment, ungapped alignment, gapped alignment, pairing), and generating features S126 derived from compositional and/or functional aspects of the microbiome associated with a biological sample.

Performing the sequencing analysis operation S124 with identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases.

Additionally or alternatively, in relation to generating a microbiome functional diversity dataset, Block S120 can include extracting candidate features associated with functional aspects of one or more microbiome components of the aggregate set of biological samples S127, as indicated in the microbiome composition dataset. Extracting candidate functional features can include identifying functional features associated with one or more of: prokaryotic clusters of orthologous groups of proteins (COGs); eukaryotic clusters of orthologous groups of proteins (KOGs); any other suitable type of gene product; an RNA processing and modification functional classification; a chromatin structure and dynamics functional classification; an energy production and conversion functional classification; a cell cycle control and mitosis functional classification; an amino acid metabolism and transport functional classification; a nucleotide metabolism and transport functional classification; a carbohydrate metabolism and transport functional classification; a coenzyme metabolism functional classification; a lipid metabolism functional classification; a translation functional classification; a transcription functional classification; a replication and repair functional classification; a cell wall/membrane/envelop biogenesis functional classification; a cell motility functional classification; a post-translational modification, protein turnover, and chaperone functions functional classification; an inorganic ion transport and metabolism functional classification; a secondary metabolites biosynthesis, transport and catabolism functional classification; a signal transduction functional classification; an intracellular trafficking and secretion functional classification; a nuclear structure functional classification; a cytoskeleton functional classification; a general functional prediction only functional classification; and a function unknown functional classification; and any other suitable functional classification.

Additionally or alternatively, extracting candidate functional features in Block S127 can include identifying functional features associated with one or more of: systems information (e.g., pathway maps for cellular and organismal functions, modules or functional units of genes, hierarchical classifications of biological entities); genomic information (e.g., complete genomes, genes and proteins in the complete genomes, ortholog groups of genes in the complete genomes); chemical information (e.g., chemical compounds and glycans, chemical reactions, enzyme nomenclature); health information (e.g., human diseases, approved drugs, crude drugs and health-related substances); metabolism pathway maps; genetic information processing (e.g., transcription, translation, replication and repair, etc.) pathway maps; environmental information processing (e.g., membrane transport, signal transduction, etc.) pathway maps; cellular processes (e.g., cell growth, cell death, cell membrane functions, etc.) pathway maps; organismal systems (e.g., immune system, endocrine system, nervous system, etc.) pathway maps; human disease pathway maps; drug development pathway maps; and any other suitable pathway map.

In extracting candidate functional features, Block S127 can comprise performing a search of one or more databases, such as the Kyoto Encyclopedia of Genes and Genomes (KEGG) and/or the Clusters of Orthologous Groups (COGs) database managed by the National Center for Biotechnology Information (NCBI). Searching can be performed based upon results of generation of the microbiome composition dataset from one or more of the set of aggregate biological samples. Searching can additionally or alternatively be performed according to any other suitable filters. In specific examples, Block S127 can include extracting candidate functional features, based on the microbiome composition dataset, from a KEGG database resource and a COG database resource; however, Block S127 can comprise extracting candidate functional features in any other suitable manner.

Upon identification of represented groups of microorganisms of the microbiome associated with a biological sample and/or identification of candidate functional aspects (e.g., functions associated with the microbiome components of the biological samples), generating features derived from compositional and/or functional aspects of the microbiome associated with the aggregate set of biological samples can be performed.

In one variation, generating features can include generating features derived from multilocus sequence typing (MLST), which can be performed experimentally at any stage in relation to implementation of the methods 100, 200, in order to identify markers useful for characterization in subsequent blocks of the method 100. Additionally or alternatively, generating features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g., involving pairs, triplets), correlative (e.g., related to correlations between different features), and/or related to changes in features (i.e., temporal changes, changes across sample sites, etc., spatial changes, etc.). Features can, however, be generated in any other suitable manner in Block S120.

1.3 First Method: Supplementary Data

Block S130 recites: receiving a supplementary dataset, associated with at least a subset of the population of subjects, wherein the supplementary dataset is informative of characteristics associated with the immune microbial dysfunction. Block S130 functions to acquire additional data associated with one or more subjects of the set of subjects, which can be used to train and/or validate the characterization processes performed in Block S140. In Block S130, the supplementary dataset preferably includes survey-derived data, but can additionally or alternatively include any one or more of: contextual data derived from sensors, medical data (e.g., current and historical medical data), and any other suitable type of data. In variations of Block S130 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset received in Block S130 can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, etc.), biometric data (e.g., data recorded through sensors within the patient's mobile computing device, data recorded through a wearable or other peripheral device in communication with the patient's mobile computing device), location data (e.g., using GPS elements), and any other suitable data. Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S130 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement Block S130.

1.4 First Method: Characterizations of the Immune Microbial Dysfunction

Block S140 recites: generating a characterization of the immune microbial dysfunction based upon the supplementary dataset and features extracted from at least one of the microbiome composition dataset and the microbiome functional diversity dataset. Block S140 functions to perform a characterization process for identifying features and/or feature combinations that can be used to characterize subjects or groups with the immune microbial dysfunction based upon their microbiome composition and/or functional features. Additionally or alternatively, the characterization process can be used as a diagnostic tool that can characterize a subject (e.g., in terms of behavioral traits, in terms of medical conditions, in terms of demographic traits, etc.) based upon their microbiome composition and/or functional features, in relation to other health condition states, behavioral traits, medical conditions, demographic traits, and/or any other suitable traits. Such characterization can then be used to suggest or provide personalized therapies by way of the therapy model of Block S150.

In performing the characterization process, Block S140 can use computational methods (e.g., statistical methods, machine learning methods, artificial intelligence methods, bioinformatics methods, etc.) to characterize a subject as exhibiting features characteristic of a group of subjects with the immune microbial dysfunction.

In one variation, characterization can be based upon features derived from a statistical analysis (e.g., an analysis of probability distributions) of similarities and/or differences between a first group of subjects exhibiting a target state (e.g., a health condition state) associated with the immune microbial dysfunction, and a second group of subjects not exhibiting the target state (e.g., a "normal" state) associated with the immune microbial dysfunction. In implementing this variation, one or more of a Kolmogorov-Smirnov (KS) test, a permutation test, a Cramér-von Mises test, and any other statistical test (e.g., t-test, Welch's t-test, z-test, chi-squared test, test associated with distributions, etc.) can be used. In particular, one or more such statistical hypothesis tests can be used to assess a set of features having varying degrees of abundance in a first group of subjects exhibiting a target state (i.e., an adverse state) associated with the immune microbial dysfunction and a second group of subjects not exhibiting the target state (i.e., having a normal state) associated with the immune microbial dysfunction. In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of microorganism and/or presence of a functional feature that is abundant in a certain percentage of subjects of the first group and subjects of the second group, wherein a relative abundance of the taxon between the first group of subjects and the second group of subjects can be determined from a KS test or a Welch's t-test, with an indication of significance (e.g., in terms of p-value). Thus, an output of Block S140 can comprise a normalized relative abundance value (e.g., 25% greater abundance of a taxon-derived feature and/or a functional feature in sick subjects vs. healthy subjects) with an indication of significance (e.g., a p-value of 0.0013). Variations of feature generation can additionally or alternatively implement or be derived from functional features or metadata features (e.g., non-bacterial markers).

In performing the characterization process, Block S140 can additionally or alternatively transform input data from at least one of the microbiome composition dataset and microbiome functional diversity dataset into feature vectors that can be tested for efficacy in predicting characterizations of the population of subjects. Data from the supplementary dataset can be used to inform characterizations of the immune microbial dysfunction, wherein the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with presence of the immune microbial dysfunction.

In variations, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset and/or the supplementary dataset. Additionally, combinations of features can be used in a feature vector, wherein features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

Figure 4:
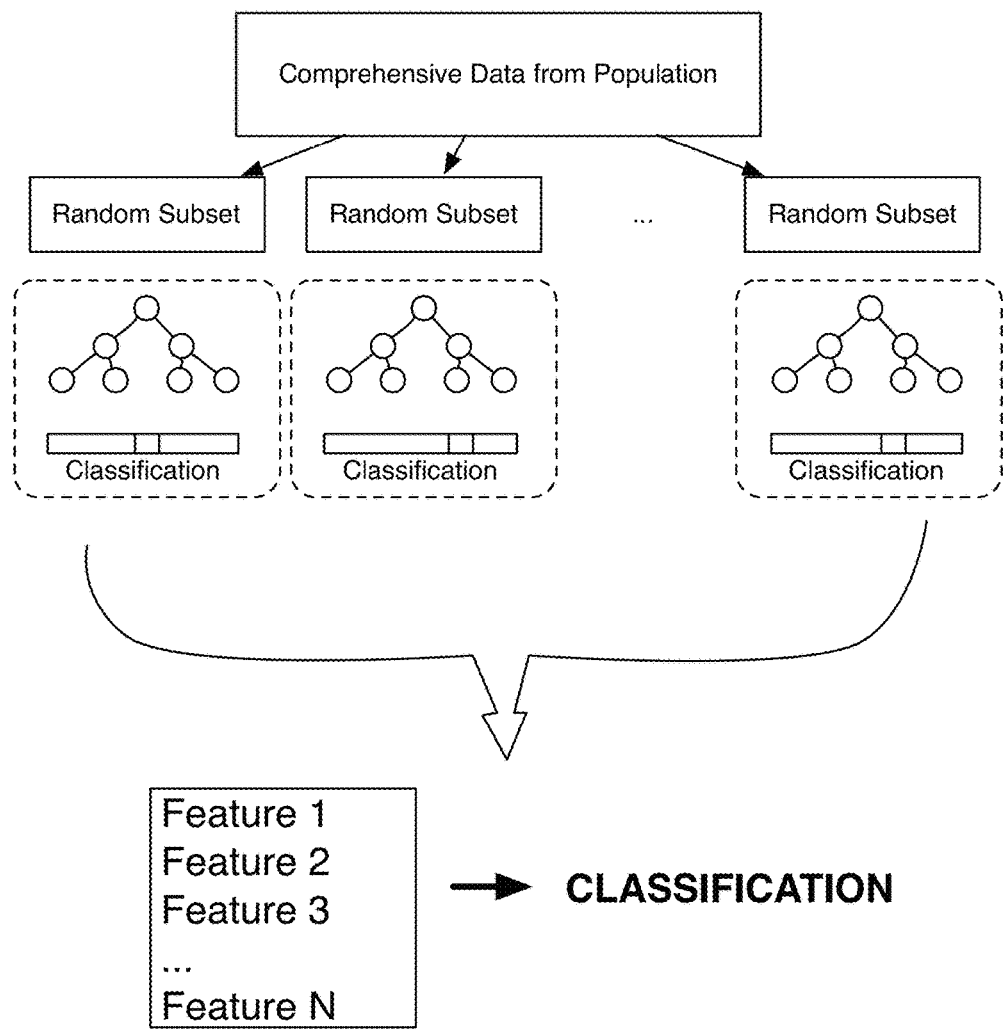
FIG. 4 depicts a variation of a process for generation of a model in an embodiment of a method and system for generating microbiome-derived diagnostics and therapeutics.

As shown in FIG. 4, in one such alternative variation of Block S140, the characterization process can be generated and trained according to a random forest predictor (RFP) algorithm that combines bagging (i.e., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

1.4.1 Crohn's Disease Characterization

In one implementation, a characterization process of Block S140 based upon statistical analyses can identify the sets of features that have the highest correlations with Crohn's disease, for which one or more therapies would have a positive effect, based upon an algorithm trained and validated with a validation dataset derived from a subset of the population of subjects. In particular, Crohn's disease in this first variation is a gastrointestinal disorder typically diagnosed based on one or more of: colonoscopy-based methods, endoscopy-based methods (e.g., capsule endoscopy), and computed tomography (CT) scans to observe multinucleated giant cells. In the first variation, a set of features useful for diagnostics associated with Crohn's disease includes features derived from one or more of the following taxa: *Clostridium* (genus), *Flavonifractor* (genus), *Prevotella* (genus), Clostridiaceae (family), Prevotellaceae (family), Oscillospiraceae (family), Gammaproteobacteria (class), and Proteobacteria (phylum). Additionally or alternatively, the set of features can be derived from one or more of the following taxa: *Eggerthella* (genus), *Akkermansia* (genus), *Anaerosporobacter* (genus), *Erysipelothrix* (genus), *Legionella* (genus), *Parabacteroides* (genus), *Odoribacter* (genus), *Barnesiella* (genus), *Actinobacillus* (genus), *Clostridium* (genus), *Haemophilus* (genus), *Veillonella* (genus), *Bacteroides* (genus), *Megasphaera* (genus), *Marvinbryantia* (genus), *Butyricicoccus* (genus), *Bilophila* (genus), *Oscillibacter* (genus), *Butyricimonas* (genus), *Ruminococcus* (genus), *Sarcina* (genus), *Lactobacillus* (genus), *Streptococcus* (genus), *Pectobacterium* (genus), *Coprococcus* (genus), *Eubacterium* (genus), *Collinsella* (genus), *Faecalibacterium* (genus), *Subdoligranulum* (genus), and *Cronobacter* (genus).

Additionally or alternatively, the set of features associated with Crohn's disease can be derived from one or more of: a COG (D) code (e.g., a cell cycle control, cell division, and chromosome partitioning functional feature); a COG (I) code (e.g., a lipid transport and metabolism functional feature); a COG (J) code (e.g., a translation, ribosomal structure and biogenesis functional feature); a cell growth and death KEGG pathway derived feature; an endocrine system KEGG pathway derived feature; a folding, sorting, and degradation KEGG pathway derived feature; a metabolism KEGG pathway derived feature; a metabolism of terpenoids and polyketides KEGG pathway derived feature; a replication and repair KEGG pathway derived feature; a translation KEGG pathway derived feature; an amino acid related enzymes KEGG pathway derived feature; an aminoacyl-tRNA biosynthesis KEGG pathway derived feature; a homologous recombination KEGG pathway derived feature; a nucleotide excision repair KEGG pathway derived feature; a PPAR signaling pathway KEGG pathway derived feature; a peptidoglycan biosynthesis KEGG pathway derived feature; a prion diseases KEGG pathway derived feature; a ribosome KEGG pathway derived feature; a translation factors KEGG pathway derived feature; a large subunit ribosomal protein L20 KEGG derived feature (e.g., K02887 KEGG code associated with RP-L20, MRPL20, and/or rpIT); a $Mg^{2+}$-importing ATPase [EC:2.6.3.2] KEGG derived feature (e.g., a K01531 KEGG code associated with mgtA and/or mgtB); a peptidyl-tRNA hydrolase PTH1 family [EC:3.1.1.29] KEGG derived feature (e.g., a K01056 KEGG code associated with PTH1, pth, and/or spoVC); a large subunit ribosomal protein L13 KEGG derived feature (e.g., a K02871 KEGG code associated with RP-L13, MRPL13, and/or rpIM); a type IV pilus assembly protein PilQ KEGG derived feature (e.g., a K02666 KEGG code associated with pilQ, where pilus allows attachment of bacterial cells to the gut wall); a superoxide dismutase, Cu—Zn family [EC:1.15.1.1] KEGG derived feature (e.g., a K04565 KEGG code associated with SOD1); a transposase KEGG derived feature (e.g., a K07487 KEGG code associated with transposases that catalyze the replicative transposition of transposable elements); and a transposase IS30 family KEGG derived feature (e.g., a K07482 KEGG code associated with transposases that catalyze the replicative transposition of transposable elements). Thus, characterization of the subject comprises characterization of the subject as someone with Crohn's disease based upon detection of one or more of the above features, in a manner that is an alternative or supplemental to typical methods of diagnosis. In variations of the specific example, the set of features can, however, include any other suitable features useful for diagnostics.

1.4.2 IBS Characterization

In another implementation, a characterization process of Block S140 based upon statistical analyses can identify the sets of features that have the highest correlations with irritable bowel syndrome (IBS), for which one or more therapies would have a positive effect, based upon an algorithm trained and validated with a validation dataset derived from a subset of the population of subjects. In particular, IBS in this first variation is a gastrointestinal disorder characterized by chronic abdominal pain, discomfort, bloating, and alteration of bowel habits, as typically assessed by colonscopy and exclusion of other gastrointestinal disorders (e.g., Celiac disease). In the first variation, a set of features useful for diagnostics associated with IBD includes features derived from one or more of the following taxa: *Flavonifractor* (genus), *Odoribacter* (genus), *Blautia* (genus), and *Finegoldia* (genus). Additionally or alternatively, a set of features can be derived from one or more of the following taxa: *Flavonifractor plautii* (species), *Holdemania* (genus), *Bacteroides* (genus), Bacteroidaceae (family), *Alistipes* (genus), Rikenellaceae (family), *bacterium* NLAE-zl-P827 (species), Deltaproteobacteria (class), *Bilophila* (genus), Pasteurellaceae (family), Pasteurellales (order), Gammaproteobacteria (class), *Bilophila wadsworthia* (species), Clostridiales (order), Clostridia (class), *Odoribacter* (genus), *Clostridium lavalense* (species), *Odoribacter splanchnicus* (species), Coriobacteriaceae (family), Rhodospirillales (order), organismal metagenomes (no rank), *Anaerostipes* (genus), Actinobacteria (class), Prevotellaceae (family), Rhodospirillaceae (family), *bacterium* NLAE-zl-H54 (species), Actinobacteridae spp. (no rank), *Roseburia* sp. 11SE38 (species), Bifidobacteriaceae (family), Bifidobacteriales (order), *Bifidobacterium* (genus), butyrate-producing *bacterium* SR1/1 (species), *Finegoldia magna* (species), *Finegoldia* (genus), and *Peptoniphilus* (genus).

Additionally or alternatively, the set of features associated with IBS can be derived from one or more of: pcoC KEGG derived feature (e.g., a K07156 KEGG code); a carboxylate-amine ligase [EC:6.3.-.-] KEGG derived feature (e.g., a K06048 KEGG code associated with ybdK); and an isocitrate lyase [EC:4.1.3.1] KEGG derived feature (e.g., a K01637 KEGG code associated with aceA). Thus, characterization of the subject comprises characterization of the subject as someone with IBS based upon detection of one or more of the above features, in a manner that is an alternative or supplemental to typical methods of diagnosis. In variations of the specific example, the set of features can, however, include any other suitable features useful for diagnostics.

1.4.3 IBD Characterization

In another implementation, a characterization process of Block S140 based upon statistical analyses can identify the sets of features that have the highest correlations with inflammatory bowel disease (IBD), for which one or more therapies would have a positive effect, based upon an algorithm trained and validated with a validation dataset derived from a subset of the population of subjects. In particular, IBD in this first variation is a gastrointestinal disorder characterized by biopsy on colonoscopy and/or fecal calprotectin. In the first variation, a set of features useful for diagnostics associated with IBD includes features derived from one or more of the following taxa: *Clostridium* (genus), *Ruminococcus* (genus), Clostridiaceae (family), Veillonellaceae (family), Selenomonadales (order), Gammaproteobacteria (class), Negativicutes (class), and Proteobacteria (phylum). Additionally or alternatively, a set of features can be derived from one or more of the following taxa: *bacterium* NLAE-zl-P562 (species), *Actinobacillus porcinus* (species), *Megasphaera* (genus), *Actinobacillus* (genus), *Flavonifractor plautii* (species), Pasteurellaceae (family), Pasteurellales (order), Gammaproteobacteria (class), Enterobacteriales (order), Enterobacteriaceae (family), Veillonellaceae (family), *Bacteroides fragilis* (species), Lactobacillales (order), Proteobacteria (phylum), Selenomonadales (order), Negativicutes (class), Streptococcaceae (family), Bacilli (class), *Cronobacter* (genus), *Cronobacter sakazakii* (species), *Streptococcus* (genus), Burkholderiales (order), Betaproteobacteria (class), Sutterellaceae (family), Erysipelotrichaceae (family), Erysipelotrichia (class), Erysipelotrichales (order), uncultured *Coriobacteriia bacterium* (species), Coriobacteriales (order), Coriobacteriaceae (family), *Collinsella* (genus), *Holdemania* (genus), *Roseburia* (genus), Ruminococcaceae (family), Deltaproteobacteria (class), *Pseudobutyrivibrio* (genus), delta/epsilon subdivisions (subphylum), Desulfovibrionales (order), Christensenellaceae (family), Porphyromonadaceae (family), Acidaminococcaceae (family), *Ruminococcus* (genus), *Marvinbryantia* (genus), Chlamydiae/Verrucomicrobia group (superphylum), butyrate-producing *bacterium* SR1/1 (species), Sphingobacteriales (order), Bacillales (order), Bacillales incertae sedis (no rank), Bacillales Family XI. Incertae Sedis (no rank), and Oceanospirillales (order).

Additionally or alternatively, the set of features associated with IBD can be derived from one or more of: a replication and repair KEGG pathway derived feature; a UDP-N-acetyl-D-glucosamine dehydrogenase [EC:1.1.1.136] KEGG derived feature (e.g., a K130015 KEGG code associated with wbpA); a putative glycerol-1-phosphate prenyltransferase [EC:2.5.1.-] KEGG derived feature (e.g., a K07094 KEGG code associated with pcrB); a hypothetical protein KEGG derived feature (e.g., a K07501 KEGG code); a proline dehydrogenase [EC:1.5.-.-] KEGG derived feature (e.g., a K00318 KEGG code associated with PRODH); and a transposase IS30 family KEGG derived feature (e.g., a K07482 code associated with transposases that catalyze the replicative transposition of transposable elements).

Thus, characterization of the subject comprises characterization of the subject as someone with IBD based upon detection of one or more of the above features, in a manner that is an alternative or supplemental to typical methods of diagnosis. In variations of the specific example, the set of features can, however, include any other suitable features useful for diagnostics.

1.4.4 Ulcerative Colitis Characterization

In another implementation, a characterization process of Block S140 based upon statistical analyses can identify the sets of features that have the highest correlations with ulcerative colitis, for which one or more therapies would have a positive effect, based upon an algorithm trained and validated with a validation dataset derived from a subset of the population of subjects. In particular, Ulcerative colitis in this first variation is a gastrointestinal disorder typically characterized by one or more of: a complete blood count, electrolyte studies, renal function tests, liver function tests, x-ray imaging, urinalysis, C-reactive protein measurement, and sigmoidoscopy. In the first variation, a set of features useful for diagnostics associated with ulcerative colitis includes features derived from one or more of the following taxa: *Clostridium* (genus), *Lachnospira* (genus), *Blautia* (genus), *Dialister* (genus), *Ruminococcus* (genus), Clostridiaceae (family), Peptostreptococcaceae (family), Veillonellaceae (family), Erysipelotrichaceae (family), Christensenellaceae (family), Erysipelotrichales (order), Gammaproteobacteria (class), and Erysipelotrichia (class). Additionally or alternatively, a set of features can be derived from one or more of the following taxa: *Actinobacillus porcinus* (species), *Actinobacillus* (genus), Pasteurellaceae (family), Pasteurellales (order), Gammaproteobacteria (class), *Flavonifractor plautii* (species), *Flavonifractor* (genus), Lactobacillales (order), *Lachnospiraceae bacterium 2_1_58FAA* (species), Bacilli (class), Veillonellaceae (family), *bacterium* NLAE-zl-P430 (species), *Dialister* (genus), *Parasutterella* (genus), *Faecalibacterium* (genus), *Parasutterella excrementihominis* (species), *Collinsella* (genus), Coriobacteriaceae (family), uncultured *Coriobacteriia bacterium* (species), Coriobacteriales (order), *Pseudobutyrivibrio* (genus), *Bacteroides fragilis* (species), *Holdemania* (genus), Porphyromonadaceae (family), Chlamydiae/Verrucomicrobia group (superphylum), *Eggerthella lenta* (species), Verrucomicrobia (phylum), Bacteroidales (order), Bacteroidia (class), Bacteroidetes (phylum), Bacteroidetes/Chlorobi group (superphylum), Verrucomicrobiae (class), Verrucomicrobiales (order), Verrucomicrobiaceae (family), *Subdoligranulum* (genus), *Dorea* (genus), Deltaproteobacteria (class), delta/epsilon subdivisions (subphylum), Bacillales incertae sedis (no rank), Desulfovibrionales (order), *Ruminococcus* (genus), *Coprococcus* (genus), Eubacteriaceae (family), *Eubacterium* (genus), Christensenellaceae (family), Acidaminococcaceae (family), Rhodospirillales (order), *Marvinbryantia* (genus), Rhodospirillaceae (family), Bacillales (order), *Alistipes putredinis* (species), and Bacillaceae (family).

Additionally or alternatively, the set of features associated with ulcerative colitis can be derived from one or more of: a COG (B) code (e.g., chromatin structure and dynamics functional feature); a COG (I) code (e.g., a lipid transport and metabolism functional feature); a cell growth and death KEGG pathway derived feature; a metabolism of terpenoids and polyketides KEGG pathway derived feature; a signal transduction KEGG pathway derived feature; a translation KEGG pathway derived feature; a base excision repair KEGG pathway derived feature; a cell cycle—*Caulobacter* KEGG pathway derived feature; a N-Glycan biosynthesis KEGG pathway derived feature; an Oxidative phosphorylation KEGG pathway derived feature; a putative glycerol-1-phosphate prenyltransferase [EC:2.5.1.-] KEGG derived feature (e.g., a K070094 KEGG code associated with pcrB); a 5,10-methylenetetrahydromethanopterin reductase [EC:1.5.98.2] KEGG derived feature (e.g., a K00320 KEGG code associated with mer); a glutamate:$Na^+$ symporter ESS family KEGG derived feature (e.g., a K03312 KEGG code associated with gltS); a putative transposase KEGG derived feature (e.g., a K07494 KEGG code); a diacylglycerol kinase (ATP) [EC:2.7.1.107] KEGG derived feature (e.g., a K07029 KEGG code associated with dagK); an uncharacterized protein KEGG derived feature (e.g., a K06936 KEGG code); an uncharacterized protein KEGG derived feature (e.g., a K07161 KEGG code); an uncharacterized protein KEGG derived feature (e.g., a K09126 KEGG code); a LPPG:FO 2-phospho-L-lactate transferase [EC:2.7.8.28] KEGG derived feature (e.g., a K11212 KEGG code associated with cofD); and a phosphosulfolactate synthase [EC:4.4.1.19] KEGG derived feature (e.g., a K08097 KEGG code associated with comA).

Thus, characterization of the subject comprises characterization of the subject as someone with ulcerative colitis based upon detection of one or more of the above features, in a manner that is an alternative or supplemental to typical methods of diagnosis. In variations of the specific example, the set of features can, however, include any other suitable features useful for diagnostics.

1.4.5 Celiac Disease Characterization

In another implementation, a characterization process of Block S140 based upon statistical analyses can identify the sets of features that have the highest correlations with celiac disease, for which one or more therapies would have a positive effect, based upon an algorithm trained and validated with a validation dataset derived from a subset of the population of subjects. In particular, celiac disease in this first variation is an autoimmune disorder of the small intestine that causes gastrointestinal discomfort, gluten intolerance, fatigue, and nutritional deficiencies. In the first variation, a set of features useful for diagnostics associated with celiac disease includes features derived from one or more of the following taxa: *Clostridium* (genus), *Oscillibacter* (genus), *Sutterella* (genus), Clostridiaceae (family), Peptostreptococcaceae (family), Peptococcaceae (family), Oscillospiraceae (family), and Proteobacteria (phylum). Additionally or alternatively, a set of features can be derived from one or more of the following taxa: *Parasutterella* (genus), *Bacteroides uniformis* (species), *Parasutterella excrementihominis* (species), *Bacteroides fragilis* (species), Acidobacteria (phylum), *Actinobacillus* (genus), *Actinobacillus porcinus* (species), Pasteurellaceae (family), and Pasteurellales (order).

Additionally or alternatively, the set of features associated with celiac disease can be derived from one or more of: a COG (W) code (e.g., extracellular structures functional feature); a putative membrane protein KEGG derived feature (e.g., a K08996 KEGG code associated with yagU); a nitric oxide reductase subunit B [EC:1.7.2.5] KEGG derived feature (e.g., a K04561 KEGG code associated with norB); a competence protein ComGA KEGG derived feature (e.g., a K02243 KEGG code associated with comGA); a competence protein ComGC KEGG derived feature (e.g., a K02245 KEGG code associated with comGC); a DNA replication protein KEGG derived feature (e.g., a K02086 KEGG code associated with dnaD); a separation ring formation regulator KEGG derived feature (e.g., a K06286 KEGG code associated with ezrA); a glyceraldehyde-3-phosphate dehydrogenase (NADP+) [ED:1.2.1.9] KEGG derived feature (e.g., a K00131 KEGG code associated with gapN); a leader peptidase (prepilin peptidase)/N-methyltransferase [EC:3.4.23.43 2.1.1.-] (e.g., a K02236 KEGG code associated with comC); a pyruvate oxidase [EC: 1.2.3.3] KEGG derived feature (e.g., a K00158 KEGG code associated with poxL); a MFS transporter, SHS family, sialic acid transporter KEGG derived feature (e.g., a K03290 KEGG code associated with nanT); a medium-chain acyl-[acyl-carrier-protein] hydrolase [EC:3.1.2.21] KEGG derived feature (e.g., a K01071 KEGG code associated with MCH); an acyl-CoA hydrolase [EC:3.1.2.20] KEGG derived feature (e.g., a K01073 KEGG code); a glucan 1,6-alpha-glucosidase [EC:3.2.1.70] KEGG derived feature (e.g., a K01215 KEGG code associated with dexB); a putative membrane protein KEGG derived feature (e.g., a K08987 KEGG code); a hydroxymethylglutaryl-CoA reductase [EC: 1.1.1.88] KEGG derived feature (e.g., a K00054 KEGG code associated with mvaA); a penicillin-binding protein KEGG derived feature (e.g., a K03693 KEGG code associated with pbp); a competence protein CoiA KEGG derived feature (e.g., a K06198 KEGG code associated with coiA); an aminotransferase [EC:2.6.1.-] KEGG derived feature (e.g., a K00841 KEGG code associated with patA); an X-pro dipeptidyl-peptidase [EC:3.4.14.11] KEGG derived feature (e.g., a K01281 KEGG code associated with pepXP); a SprT-like protein KEGG derived feature (e.g., a K03095 KEGG code associated with sprL); a general stress protein 13 KEGG derived feature (e.g., a K07570 KEGG code associated with GSP13); a competence protein ComGF KEGG derived feature (e.g., a K02248 KEGG code associated with comGF); a penicillin-binding protein 2A [EC: 2.4.1.129 2.3.2.-] KEGG derived feature (e.g., a K12555 KEGG code associated with pbp2A); a para-aminobenzoate synthetase/4-amino-4-deoxychorismate lyase [EC:2.6.1.85 4.1.3.38] KEGG derived feature (e.g., a K03342 KEGG code associated with pabBC); an uncharacterized protein KEGG derived feature (e.g., a K09962 KEGG code); a competence protein ComFA KEGG derived feature (e.g., a K02240 KEGG code associated with comFA); and a GMP reductase [EC:1.7.1.7] KEGG derived feature (e.g., a K00364 KEGG code associated with guaC).

Thus, characterization of the subject comprises characterization of the subject as someone with celiac disease based upon detection of one or more of the above features, in a manner that is an alternative or supplemental to typical methods of diagnosis. In variations of the specific example, the set of features can, however, include any other suitable features useful for diagnostics.

Characterization of the subject(s) can additionally or alternatively implement use of a high false positive test and/or a high false negative test to further analyze sensitivity of the characterization process in supporting analyses generated according to embodiments of the method 100.

1.5 First Method: Therapy Models and Provision

As shown in FIG. 1A, in some variations, the first method 100 can further include Block S150, which recites: based upon the characterization, generating a therapy model configured to correct the immune microbial dysfunction. Block S150 functions to identify or predict therapies (e.g., probiotic-based therapies, phage-based therapies, small molecule-based therapies, etc.) that can shift a subject's microbiome composition and/or functional features toward a desired equilibrium state in promotion of the subject's health. In Block S150, the therapies can be selected from therapies including one or more of: probiotic therapies, phage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in a subject with the immune microbial dysfunction can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

For instance, in relation to the variations of immune microbial dysfunctions in Sections 1.4.1 through 1.4.5 above, therapies (e.g., probiotic therapies, bacteriophage-based therapies, etc.) can be configured to downregulate and/or upregulate microorganism populations or subpopulations (and/or functions thereof) associated with features characteristic of the immune microbial dysfunction.

Figure 5:
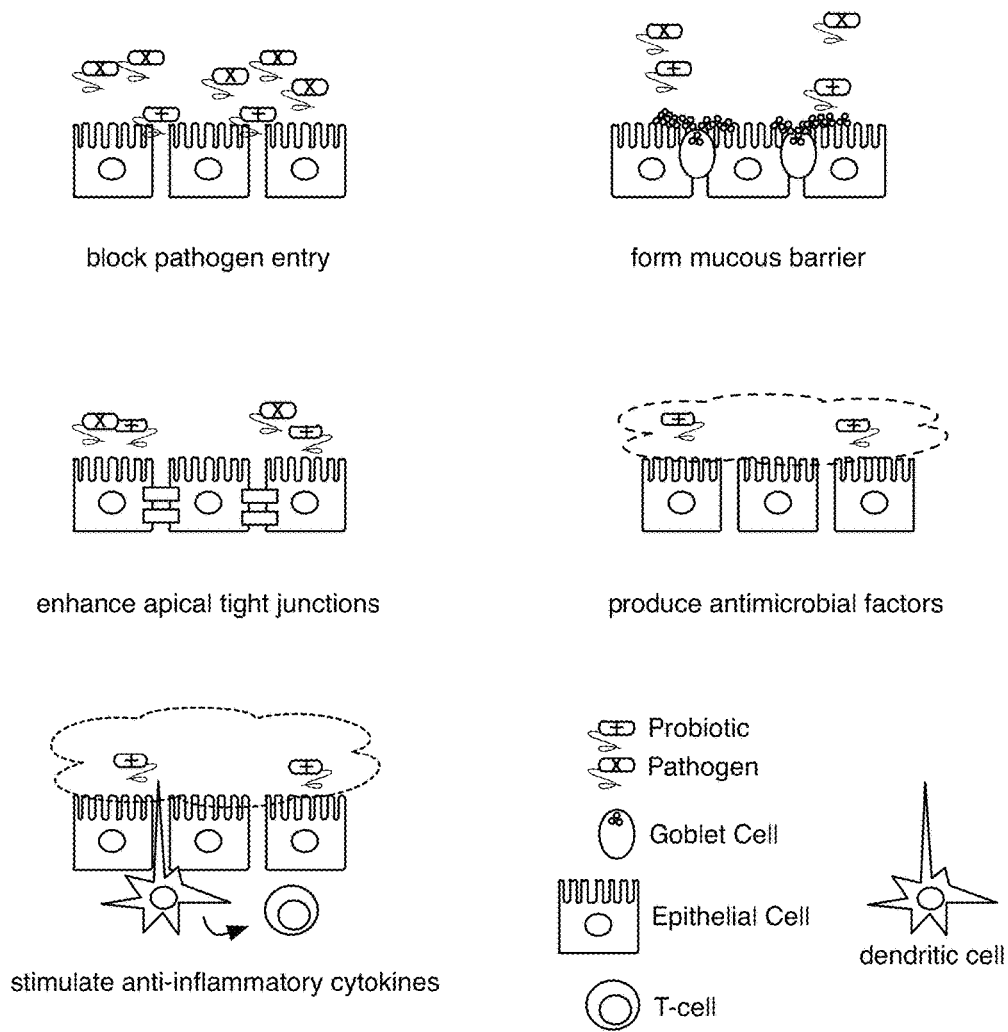
FIG. 5 depicts variations of mechanisms by which probiotic-based therapies operate in an embodiment of a method for characterizing a health condition.

In a specific example of probiotic therapies, as shown in FIG. 5, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In variations, the therapy model is preferably based upon data from a large population of subjects, which can comprise the population of subjects from which the microbiome-related datasets are derived in Block S110, wherein microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100 can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S150. Block S150 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can comprise a single type of microorganism that has an acute or moderated effect upon a subject's microbiome. Additionally or alternatively, microorganism compositions can comprise balanced combinations of multiple types of microorganisms that are configured to cooperate with each other in driving a subject's microbiome toward a desired state. For instance, a combination of multiple types of bacteria in a probiotic therapy can comprise a first bacteria type that generates products that are used by a second bacteria type that has a strong effect in positively affecting a subject's microbiome. Additionally or alternatively, a combination of multiple types of bacteria in a probiotic therapy can comprise several bacteria types that produce proteins with the same functions that positively affect a subject's microbiome.

In examples of probiotic therapies, probiotic compositions can comprise components of one or more of the identified taxa of microorganisms (e.g., as described in sections 1.4.1 through 1.4.5 above) provided at dosages of 1 million to 10 billion CFUs, as determined from a therapy model that predicts positive adjustment of a subject's microbiome in response to the therapy. Additionally or alternatively, the therapy can comprise dosages of proteins resulting from functional presence in the microbiome compositions of subjects without the immune microbial dysfunction. In the examples, a subject can be instructed to ingest capsules comprising the probiotic formulation according to a regimen tailored to one or more of his/her: physiology (e.g., body mass index, weight, height), demographics (e.g., gender, age), severity of dysbiosis, sensitivity to medications, and any other suitable factor.

Furthermore, probiotic compositions of probiotic-based therapies can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli Nissle*), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent.

Additionally or alternatively, therapies promoted by the therapy model of Block S150 can include one or more of: consumables (e.g., food items, beverage items, nutritional supplements), suggested activities (e.g., exercise regimens, adjustments to alcohol consumption, adjustments to cigarette usage, adjustments to drug usage), topical therapies (e.g., lotions, ointments, antiseptics, etc.), adjustments to hygienic product usage (e.g., use of shampoo products, use of conditioner products, use of soaps, use of makeup products, etc.), adjustments to diet (e.g., sugar consumption, fat consumption, salt consumption, acid consumption, etc.), adjustments to sleep behavior, living arrangement adjustments (e.g., adjustments to living with pets, adjustments to living with plants in one's home environment, adjustments to light and temperature in one's home environment, etc.), nutritional supplements (e.g., vitamins, minerals, fiber, fatty acids, amino acids, prebiotics, probiotics, etc.), medications, antibiotics, and any other suitable therapeutic measure.

The first method 100 can, however, include any other suitable blocks or steps configured to facilitate reception of biological samples from individuals, processing of biological samples from individuals, analyzing data derived from biological samples, and generating models that can be used to provide customized diagnostics and/or therapeutics according to specific microbiome compositions of individuals.

2. Second Method: Personalized Diagnostics and Therapeutics

In some embodiments, as noted above, outputs of the first method 100 can be used to generate diagnostics and/or provide therapeutic measures for an individual based upon an analysis of the individual's microbiome. As such, a second method 200 derived from at least one output of the first method 100 can include: receiving a biological sample from a subject S210; characterizing the subject with a form of an immune microbial dysfunction based upon processing a microbiome dataset derived from the biological sample S220; and promoting a therapy to the subject with the immune microbial dysfunction based upon the characterization and the therapy model S230.

Block S210 recites: receiving a biological sample from the subject, which functions to facilitate generation of a microbiome composition dataset and/or a microbiome functional diversity dataset for the subject. As such, processing and analyzing the biological sample preferably facilitates generation of a microbiome composition dataset and/or a microbiome functional diversity dataset for the subject, which can be used to provide inputs that can be used to characterize the individual in relation to diagnosis of the immune microbial dysfunction, as in Block S220. Receiving a biological sample from the subject is preferably performed in a manner similar to that of one of the embodiments, variations, and/or examples of sample reception described in relation to Block S110 above. As such, reception and processing of the biological sample in Block S210 can be performed for the subject using similar processes as those for receiving and processing biological samples used to generate the characterization(s) and/or the therapy provision model of the first method 100, in order to provide consistency of process. However, biological sample reception and processing in Block S2100 can alternatively be performed in any other suitable manner.

Block S220 recites: characterizing the subject with a form of an immune microbial dysfunction based upon processing a microbiome dataset derived from the biological sample. Block S220 functions to extract features from microbiome-derived data of the subject, and use the features to positively or negatively characterize the individual as having a form of immune microbial dysfunction. Characterizing the subject in Block S220 thus preferably includes identifying features and/or combinations of features associated with the microbiome composition and/or functional features of the microbiome of the subject, and comparing such features with features characteristic of subjects with the immune microbial dysfunction. Block S220 can further include generation of and/or output of a confidence metric associated with the characterization for the individual. For instance, a confidence metric can be derived from the number of features used to generate the classification, relative weights or rankings of features used to generate the characterization, measures of bias in the models used in Block S140 above, and/or any other suitable parameter associated with aspects of the characterization operation of Block S140.

In some variations, features extracted from the microbiome dataset can be supplemented with survey-derived and/or medical history-derived features from the individual, which can be used to further refine the characterization operation(s) of Block S220. However, the microbiome composition dataset and/or the microbiome functional diversity dataset of the individual can additionally or alternatively be used in any other suitable manner to enhance the first method 100 and/or the second method 200.

Block S230 recites: promoting a therapy to the subject with the immune microbial dysfunction based upon the characterization and the therapy model. Block S230 functions to recommend or provide a personalized therapeutic measure to the subject, in order to shift the microbiome composition of the individual toward a desired equilibrium state. As such, Block S230 can include correcting the immune microbial dysfunction, or otherwise positively affecting the user's health in relation to the immune microbial dysfunction. Block S230 can thus include promoting one or more therapeutic measures to the subject based upon their characterization in relation to the immune microbial dysfunction.

In Block S230, providing the therapeutic measure to the subject can include recommendation of available therapeutic measures configured to modulate microbiome composition of the subject toward a desired state. Additionally or alternatively, Block S230 can include provision of customized therapy to the subject according to their characterization (e.g., in relation to a specific type of immune microbial dysfunction). In variations, therapeutic measures can include one or more of: probiotics, bacteriophage-based therapies, consumables, suggested activities, topical therapies, adjustments to hygienic product usage, adjustments to diet, adjustments to sleep behavior, living arrangement, adjustments to level of sexual activity, nutritional supplements, medications, antibiotics, and any other suitable therapeutic measure. Therapy provision in Block S230 can include provision of notifications by way of an electronic device, through an entity associated with the individual, and/or in any other suitable manner.

Figure 6:
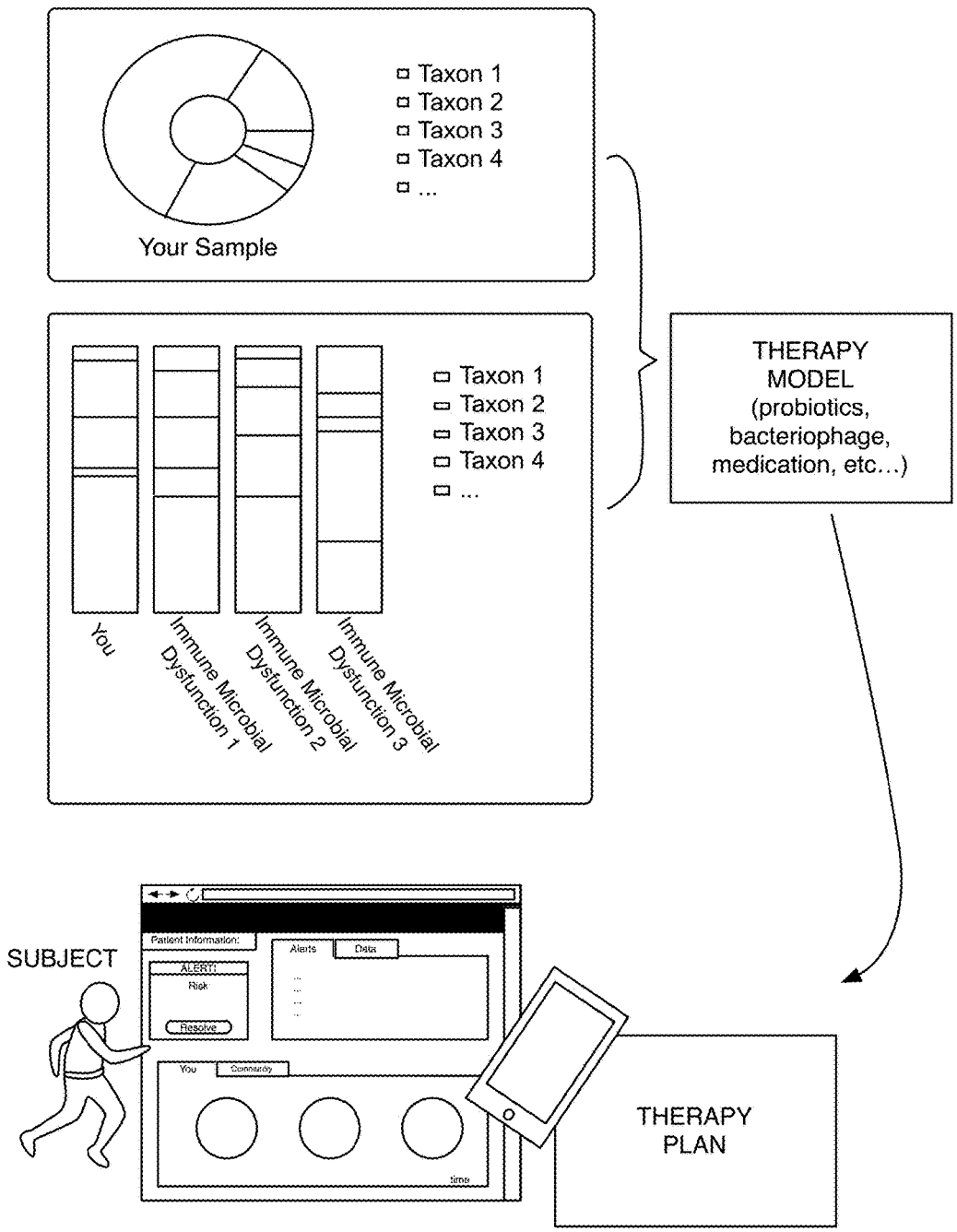
FIG. 6 depicts examples of therapy-related notification provision in an example of a method for generating microbiome-derived diagnostics and therapeutics.

In more detail, therapy provision in Block S230 can include provision of notifications to the subject regarding recommended therapeutic measures and/or other courses of action, in relation to health-related goals, as shown in FIG. 6. Notifications can be provided to an individual by way of an electronic device (e.g., personal computer, mobile device, tablet, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, wherein the user account includes information regarding the subject's characterization, detailed characterization of aspects of the subject's microbiome composition and/or functional features, and notifications regarding suggested therapeutic measures generated in Block S150. In another example, an application executing at a personal electronic device (e.g., smart phone, smart watch, head-mounted smart device) can be configured to provide notifications (e.g., at a display, haptically, in an auditory manner, etc.) regarding therapeutic suggestions generated by the therapy model of Block S150. Notifications can additionally or alternatively be provided directly through an entity associated with an subject (e.g., a caretaker, a spouse, a significant other, a healthcare professional, etc.). In some further variations, notifications can additionally or alternatively be provided to an entity (e.g., healthcare professional) associated with the subject, wherein the entity is able to administer the therapeutic measure (e.g., by way of prescription, by way of conducting a therapeutic session, etc.). Notifications can, however, be provided for therapy administration to the subject in any other suitable manner.

Furthermore, in an extension of Block S230, monitoring of the subject during the course of a therapeutic regimen (e.g., by receiving and analyzing biological samples from the subject throughout therapy, by receiving survey-derived data from the subject throughout therapy) can be used to generate a therapy-effectiveness model for each recommended therapeutic measure provided according to the model generated in Block S150.

The methods 100, 200 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for facilitating treatment of an ulcerative colitis condition for a subject, the method comprising:
   receiving a set of samples from a population of subjects comprising at least one subject associated with the ulcerative colitis condition;
   for each sample of the set of samples:
      determining a microorganism nucleic acid sequence, comprising:
         selecting a primer for a nucleic acid sequence;
         fragmenting nucleic acid material based on the sample; and
         amplifying the fragmented nucleic acid material based on the primer; and
      determining an alignment of the microorganism nucleic acid sequence to a reference nucleic acid sequence;
   generating a microbiome composition dataset and a microbiome functional diversity dataset for the population of subjects based upon the alignments;
   collecting a supplementary dataset, associated with at least a subset of the population of subjects, wherein the supplementary dataset is informative of a characteristic associated with the ulcerative colitis condition;
   generating a characterization of the ulcerative colitis condition based upon the supplementary dataset and at least one of the microbiome composition dataset and the microbiome functional diversity dataset;
   based upon the characterization, generating a therapy model that determines a therapy for correcting the ulcerative colitis condition; and
   at an output device associated with the subject, providing the therapy to the subject with the ulcerative colitis condition based upon the characterization and the therapy model.

2. The method of claim 1, further comprising:
   providing a set of sampling kits to the population of subjects, each sampling kit of the set of sampling kits comprising a sample container configured to receive the sample from a collection site,
   wherein determining the microorganism nucleic acid sequence comprises determining the microorganism nucleic acid sequence with a bridge amplification substrate of a next generation sequencing platform of a sample processing system, and
   wherein generating the microbiome composition dataset and the microbiome functional diversity dataset comprises generating the microbiome composition dataset and the microbiome functional diversity dataset at computing devices operable to communicate with the next generation sequencing platform.

3. The method of claim 2, wherein determining the microorganism nucleic acid sequence comprises performing, at a library preparation subsystem of the sample processing system, multiplex amplification with the fragmented nucleic acid material based on the primer.

4. The method of claim 1, wherein selecting the primer comprises selecting the primer for a transposase sequence associated with the ulcerative colitis condition.

5. The method of claim 1, wherein generating the characterization of the ulcerative colitis condition comprises generating the characterization based on a set of microbiome composition features extracted from the microbiome composition dataset, wherein the set of microbiome composition features is associated with a set of taxa comprising at least one of: *Clostridium* (genus), *Lachnospira* (genus), *Blautia* (genus), *Dialister* (genus), *Ruminococcus* (genus), Clostridiaceae (family), Peptostreptococcaceae (family), Veillonellaceae (family), Erysipelotrichaceae (family), Christensenellaceae (family), Erysipelotrichales (order), Gammaproteobacteria (class), and Erysipelotrichia (class).

6. The method of claim 5, further comprising:
determining a modulator of a biomolecule associated with the set of taxa and the ulcerative colitis condition; and
deriving a therapeutic composition for the ulcerative colitis condition based on the modulator,
wherein providing the therapy comprises providing the therapeutic composition to the subject based upon the characterization and the therapy model.

7. The method of claim 5, wherein the set of microbiome composition features is associated with the set of taxa further comprising at least one of: *Actinobacillus porcinus* (species), *Actinobacillus* (genus), Pasteurellaceae (family), Pasteurellales (order), Gammaproteobacteria (class), *Flavonifractor plautii* (species), *Flavonifractor* (genus), Lactobacillales (order), *Lachnospiraceae bacterium* 2_1_58FAA (species), Bacilli (class), Veillonellaceae (family), *bacterium NLAE-zl-P$_{430}$* (species), *Dialister* (genus), *Parasutterella* (genus), *Faecalibacterium* (genus), *Parasutterella excrementihominis* (species), *Collinsella* (genus), Coriobacteriaceae (family), uncultured *Coriobacteriia bacterium* (species), Coriobacteriales (order), *Pseudobutyrivibrio* (genus), *Bacteroides fragilis* (species), *Holdemania* (genus), Porphyromonadaceae (family), Chlamydiae/Verrucomicrobia group (superphylum), *Eggerthella lenta* (species), Verrucomicrobia (phylum), Bacteroidales (order), Bacteroidia (class), Bacteroidetes (phylum), Bacteroidetes/Chlorobi group (superphylum), Verrucomicrobiae (class), Verrucomicrobiales (order), Verrucomicrobiaceae (family), *Subdoligranulum* (genus), *Dorea* (genus), Deltaproteobacteria (class), delta/epsilon subdivisions (subphylum), Bacillales incertae sedis (no rank), Desulfovibrionales (order), *Ruminococcus* (genus), *Coprococcus* (genus), Eubacteriaceae (family), *Eubacterium* (genus), Christensenellaceae (family), Acidaminococcaceae (family), Rhodospirillales (order), *Marvinbryantia* (genus), Rhodospirillaceae (family), Bacillales (order), *Alistipes putredinis* (species), and Bacillaceae (family).

8. The method of claim 5, wherein generating the characterization of the ulcerative colitis condition comprises generating the characterization based on the set of microbiome composition features and a set of microbiome functional diversity features extracted from the microbiome functional diversity dataset, wherein the set of microbiome functional diversity features comprise at least one of: a COG (B) code derived feature, a COG (I) code derived feature, a cell growth and death KEGG pathway derived feature, a metabolism of terpenoids and polyketides KEGG pathway derived feature, a signal transduction KEGG pathway derived feature, a translation KEGG pathway derived feature, a base excision repair KEGG pathway derived feature, a cell cycle—*Caulobacter* KEGG pathway derived feature, a N-Glycan biosynthesis KEGG pathway derived feature, an Oxidative phosphorylation KEGG pathway derived feature, a putative glycerol-1-phosphate prenyltransferase KEGG derived feature, a 5,10-methylenetetrahydromethanopterin reductase KEGG derived feature, a glutamate:Na$^+$ symporter ESS family KEGG derived feature, a putative transposase KEGG derived feature, a diacylglycerol kinase KEGG derived feature, an uncharacterized protein KEGG derived feature, a LPPG:FO 2-phospho-L-lactate transferase KEGG derived feature, and a phosphosulfolactate synthase KEGG derived feature.

9. The method of claim 1, wherein generating the characterization comprises analyzing a set of features extracted from the microbiome composition dataset based on a statistical analysis, wherein the set of features comprises features associated with at least one of: relative abundance of different taxonomic groups represented in the microbiome composition dataset, interactions between different taxonomic groups represented in the microbiome composition dataset, and phylogenetic distance between taxonomic groups represented in the microbiome composition dataset.

10. The method of claim 9, wherein the set of features is associated with the population of subjects comprising a first subset exhibiting the ulcerative colitis condition and a second subset not exhibiting the ulcerative colitis condition,
wherein collecting the supplementary dataset comprises collecting an ulcerative colitis diagnosis dataset generated based on at least one of: a blood test, an electrolyte study, a renal function test, a liver function test, and x-ray imaging,
wherein generating the characterization comprises correlating the set of features to the first subset of the population of subjects and the second subset of the population of subjects based on the ulcerative colitis diagnosis dataset.

11. A method for characterizing an ulcerative colitis condition for a subject, the method comprising:
for a sample of a set of samples associated with a set of subjects comprising at least one subject associated with the ulcerative colitis condition:
determining a microorganism nucleic acid sequence, comprising:
selecting a primer for a nucleic acid sequence;
fragmenting nucleic acid material based on the sample; and
amplifying the fragmented nucleic acid material based on the primer; and
determining an alignment of the microorganism nucleic acid sequence to a reference nucleic acid;
generating a microbiome feature dataset associated with the set of subjects, based on the alignment;
receiving a supplementary dataset, associated with at least a subset of the set of subjects, wherein the supplementary dataset is informative of characteristics associated with the ulcerative colitis condition;
generating a characterization of the ulcerative colitis condition based upon the supplementary dataset and the microbiome feature dataset;
based upon the characterization, determining a therapy for the subject; and
providing the therapy to the subject, wherein the therapy is operable to modulate at least one selected from a group of a microbiome composition and a microbiome function of the subject in association with the ulcerative colitis condition.

12. The method of claim 11, further comprising:
determining a cause for the ulcerative colitis condition based on the supplementary dataset and the microbiome feature dataset,
wherein providing the therapy to the subject comprises providing the therapy based on the cause for the ulcerative colitis condition.

13. The method of claim 12, wherein providing the therapy based on the cause comprises providing a consumable to the subject, wherein the consumable is operable to affect a microorganism component that selectively supports a population size adjustment of a desired taxon associated with correction of the ulcerative colitis condition.

14. The method of claim 11, wherein the microbiome feature dataset comprises a set of microbiome composition features, and wherein generating the characterization of the ulcerative colitis condition comprises generating the characterization based on the set of microbiome composition features associated with a set of taxa comprising at least one of: *Clostridium* (genus), *Lachnospira* (genus), *Blautia* (genus), *Dialister* (genus), and *Ruminococcus* (genus).

15. The method of claim 14, wherein the microbiome feature dataset comprises a set of microbiome functional diversity features, and wherein generating the characterization of the ulcerative colitis condition comprises generating the characterization based on the set of microbiome composition features and the set of microbiome functional diversity features, wherein the set of microbiome functional diversity features comprises: a clusters of orthologous groups of proteins (COG) feature set and a Kyoto Encyclopedia of Genes and Genomes (KEGG) feature set.

16. The method of claim 15,
wherein the COG feature set comprises at least one of: a COG (B) code derived feature and a COG (I) code derived feature, and
wherein the KEGG feature set comprises at least one of: a cell growth and death KEGG pathway derived feature, a metabolism of terpenoids and polyketides KEGG pathway derived feature, a signal transduction KEGG pathway derived feature, a translation KEGG pathway derived feature, a base excision repair KEGG pathway derived feature, a cell cycle—*Caulobacter* KEGG pathway derived feature, a N-Glycan biosynthesis KEGG pathway derived feature, an Oxidative phosphorylation KEGG pathway derived feature, a putative glycerol-1-phosphate prenyltransferase KEGG derived feature, a 5,10-methylenetetrahydromethanopterin reductase KEGG derived feature, a glutamate:Na$^+$ symporter ESS family KEGG derived feature, a putative transposase KEGG derived feature, a diacylglycerol kinase KEGG derived feature, an uncharacterized protein KEGG derived feature, a LPPG:FO 2-phospho-L-lactate transferase KEGG derived feature, and a phosphosulfolactate synthase KEGG derived feature.

17. The method of claim 16, wherein providing the therapy comprises providing at least one of a probiotic therapy and a prebiotic therapy to the subject, wherein the at least one of the probiotic therapy and the prebiotic therapy is operable to selectively modulate a population size of a desired taxon associated with at least one of the set of microbiome composition features and associated with at least one of the COG feature set and the KEGG feature set.

18. The method of claim 11, further comprising:
after providing the therapy, receiving a post-therapy sample from the subject;
processing the post-therapy sample; and
generating a post-therapy characterization of the subject in relation to the ulcerative colitis condition and the therapy based on the processed post-therapy sample.

19. The method of claim 18, further comprising:
determining post-therapy microbiome composition features and post-therapy microbiome functional diversity features associated with the subject, based on the processed post-therapy sample;
determining an updated therapy for the subject based on a therapy model, the post-therapy microbiome composition features, and the post-therapy microbiome functional diversity features; and
providing the updated therapy to the subject, wherein the updated therapy is operable to facilitate modification of the microbiome composition and a microbiome functional diversity of the subject for improving the ulcerative colitis condition.

20. The method of claim 19, further comprising:
updating the therapy model based on the post-therapy characterization of the subject in relation to the ulcerative colitis condition;
in response to updating the therapy model, updating a second therapy for a second user based on the updated therapy model; and
providing the updated second therapy to the second user for the ulcerative colitis condition.

* * * * *